US00PP27026P3

(12) United States Plant Patent
NeSmith

(10) Patent No.: US PP27,026 P3
(45) Date of Patent: Aug. 9, 2016

(54) SOUTHERN HIGHBUSH BLUEBERRY PLANT NAMED 'TH-906'

(50) Latin Name: ***Vaccinium corymbosum* L**
Varietal Denomination: TH-906

(71) Applicant: University of Georgia Research Foundation, Inc., Athens, GA (US)

(72) Inventor: D. Scott NeSmith, Molena, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 93 days.

(21) Appl. No.: 14/544,269

(22) Filed: Dec. 15, 2014

(65) Prior Publication Data

US 2016/0174427 P1 Jun. 16, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Annette Para
(74) *Attorney, Agent, or Firm* — Klarquist Sparkman, LLP

(57) ABSTRACT

The new variety 'TH-906' ripens in mid-May in southern Georgia. The fruit of the new variety 'TH-906' are medium to large, with good scar, and have good firmness and flavor. The new variety 'TH-906' is vigorous with an estimated chilling requirement of about 550 hours at or below approximately 7° C. The asexually reproduced variety is reliably propagated vegetatively.

4 Drawing Sheets

STATEMENT REGARDING FEDERALLY-SPONSORED RESEARCH

This invention was made, in part, with U.S. Government support on behalf of U.S. Department of Agriculture, Hatch Act Grant No. GEO 01663. The U.S. Government has certain rights in this invention.

Latin name of the genus and species of the plant claimed: 'TH-906' is a southern highbush blueberry plant that is a *Vaccinium corymbosum* L.

Variety denomination: The new southern highbush blueberry plant claimed is of the variety denominated 'TH-906'.

BACKGROUND OF THE INVENTION

The present invention relates to the discovery of a new and distinct cultivar of southern highbush blueberry plant botanically known as a *Vaccinium corymbosum* L and herein referred to as 'TH-906', as herein described and illustrated.

The new blueberry plant variety 'TH-906' was first identified growing in a cultivated area at the Georgia Experiment Station in Griffin, Ga. in 2005. The new variety 'TH-906' is early to mid-season, ripening after the early commercial variety 'Star' (U.S. Plant Pat. No. 10,675) in south and middle Georgia, but before 'Camellia' (U.S. Plant Pat. No. 18,151). The fruit of the new variety 'TH-906' has medium to large berries, with good scar and good flavor as compared to 'Star' and 'Camellia'. The new variety 'TH-906' is vigorous with an estimated chilling requirement of about 550 hours below 45° F. when produced under typical low to mid chill production regions. Pedigree and history: 'TH-906' was selected in 2005 at the Georgia Experiment Station in Griffin, Ga., originating from a cross of 'TH-653'×'Millennia' made by Dr. Scott NeSmith in 2002. The female parent 'TH-653' is a non-patented breeding line. The male parent 'Millennia' is the subject of U.S. Plant Pat. No. 18,816. 'TH-906' was first asexually propagated in 2005 in Griffin, Ga. by softwood cuttings. Asexually propagated 'TH-906' plants, propagated by softwood cuttings, have been observed growing in Griffin, Ga. and in Alapaha, Ga. The new blueberry plant variety 'TH-906' has been shown to maintain its distinguishing characteristics through successive asexual propagations by softwood cuttings in Alapaha, Ga. and Griffith, Ga.

The selection has been tested in plantings at Alapaha and Griffin, Ga. established in 2007.

SUMMARY OF THE INVENTION

The new blueberry plant variety 'TH-906' has not been observed under all possible environmental conditions. The phenotype may vary somewhat with variations in environment and cultural practices such as temperature and light intensity without, however, any variance in genotype.

The following traits have been repeatedly observed in Alapaha and Griffin, Ga., and are determined to be the unique characteristics of the new blueberry plant variety 'TH-906':

1. Good flavor;
2. Excellent plant vigor;
3. No notable diseases or other pest problems.

Compared to its female parent 'TH-653', the new variety 'TH-906' ripens earlier than 'TH-653' and exhibits a more concentrated ripening. 'TH-906' has a better picking scar than 'TH-653'. The berries of 'TH-906' are less firm than those of 'TH-653'. Compared to its male parent 'Millennia', the new variety 'TH-906' plant is more upright and reaches a greater height than 'Millennia'. 'Millennia' tends to be a more spreading plant. 'Millennia' flowers earlier than 'TH-906'. Also, the berries of 'Millennia' are larger than the berries of 'TH-906' (for 'Millennia', typical berries are 2.3 to 2.8 g versus typical 'TH-906' berries of 1.6 to 1.8 g.

The new variety 'TH-906' can be compared to the southern highbush blueberry varieties 'Star' and 'Camellia'.

Comparison: The new variety ripens after the early variety 'Star' in south and middle Georgia, but before 'Camellia'. 'TH-906' has medium to large berries. 'TH-906' has better firmness, scar and flavor characteristics as compared to standards in Griffin and Alapaha over a 5-year period (Tables 1 and 2). Table 3 depicts berry weight, firmness and Brix for 'TH-906' as compared to several southern highbush blueberry cultivars, including 'Camellia', 'Rebel' (U.S. Plant Pat. No. 18,138), 'Star', and 'Suziblue' (U.S. Plant Pat. No. 21,167). 'TH-906' produces high quality firm fruit as apparent from the comparisons.

While the major attraction of 'TH-906' is fruit quality, the variety does have an additional favorable attribute. High quality southern highbush blueberry varieties are desirable for home gardens. 'TH-906' plants are very vigorous, making them well suited for home gardeners. No notable diseases or other pest problems have been observed in 'TH-906' that are not also common for other varieties, also making it suitable for home growing.

TABLE 1

5-year average ratings of some fruit and plant characteristics of 'TH-906' and southern highbush standard cultivars 'Camellia' and 'Star' from (2009-2013) in field test plots in Alapaha, GA. Rating scales are based on a 1 to 10 score, with 1 being the least desirable and 10 being the most desirable. A value of 6-7 is generally considered to be the minimum acceptable rating for a commercial cultivar. These plants were established in 2007.

| | Alapaha location | | |
|---|---|---|---|
| Attribute | 'Star' | 'Camellia' | 'TH-906' |
| Berry size | 7.6 ± 0.2 | 8.9 ± 0.2 | 7.6 ± 0.2 |
| Barry scar | 7.0 ± 0.1 | 7.2 ± 0.2 | 7.6 ± 0.1 |
| Berry color | 7.1 ± 0.1 | 8.7 ± 0.2 | 7.9 ± 0.1 |
| Berry firmness | 7.2 ± 0.1 | 7.2 ± 0.1 | 7.5 ± 0.3 |
| Berry flavor | 7.0 ± 0.1 | 7.8 ± 0.1 | 7.9 ± 0.2 |
| Cropping | 4.7 ± 1.7 | 5.4 ± 0.3 | 5.1 ± 0.8 |
| Plant vigor | 6.3 ± 0.2 | 9.8 ± 0.2 | 9.1 ± 0.3 |
| Date of 50% flowering | March 3 | March 11 | March 8 |
| Date of 50% ripening | May 8 | May 15 | May 12 |
| Fruit development period (days) | 66.3 ± 6.1 | 65.3 ± 4.9 | 66.0 ± 5.0 |

TABLE 2

5-year average ratings of some fruit and plant characteristics of 'TH-906' and southern highbush standard cultivars 'Camellia' and 'Star' (2009-2013) in field test plots at Griffin, GA. Rating scales are based on a 1 to 10 score, with 1 being the least desirable and 10 being the most desirable. A value of 6-7 is generally considered to be the minimum acceptable rating for a commercial cultivar. These plants were established in 2007.

| | Griffin location | | |
|---|---|---|---|
| Attribute | 'Star' | 'Camellia' | 'TH-906' |
| Berry size | 7.4 ± 0.2 | 8.6 ± 0.2 | 7.3 ± 0.2 |
| Barry scar | 6.9 ± 0.1 | 7.0 ± 0.1 | 7.1 ± 0.1 |
| Berry color | 7.1 ± 0.1 | 7.9 ± 0.2 | 7.4 ± 0.3 |
| Berry firmness | 7.2 ± 0.1 | 7.2 ± 0.1 | 7.2 ± 0.2 |
| Berry flavor | 7.1 ± 0.1 | 7.4 ± 0.2 | 7.6 ± 0.2 |
| Cropping | 6.8 ± 1.1 | 7.9 ± 0.2 | 6.5 ± 0.9 |
| Plant vigor | 8.5 ± 0.3 | 9.8 ± 0.1 | 8.5 ± 0.3 |
| Date of 50% flowering | March 13 | March 25 | March 20 |
| Date of 50% ripening | May 25 | May 31 | May 29 |
| Fruit development period (days) | 73.3 ± 10.4 | 67.3 ± 4.8 | 70.4 ± 7.5 |

TABLE 3

Berry weight, firmness, and Brix for several southern highbush blueberry cultivars and 'TH-906' grown in Griffin, GA during 2013.

| Selection or cultivar | Berry weight (g) | Berry firmness (g/mm) | Berry Brix (%) |
|---|---|---|---|
| 'Camellia' | 2.56 | 150 | 13.3 |
| 'Rebel' | 2.52 | 192 | 12.5 |
| 'Star' | 1.79 | 191 | 13.5 |
| 'Suziblue' | 2.54 | 190 | 13.7 |
| 'TH-906' | 1.70 | 209 | 13.3 |

BRIEF DESCRIPTION OF THE FIGURES

The accompanying photographic illustration shows typical specimens in full color of the foliage and fruit of the new variety 'TH-906'. The colors are as nearly true as is reasonably possible in a color representation of this type.

BOTANICAL DESCRIPTION

Figure 1:
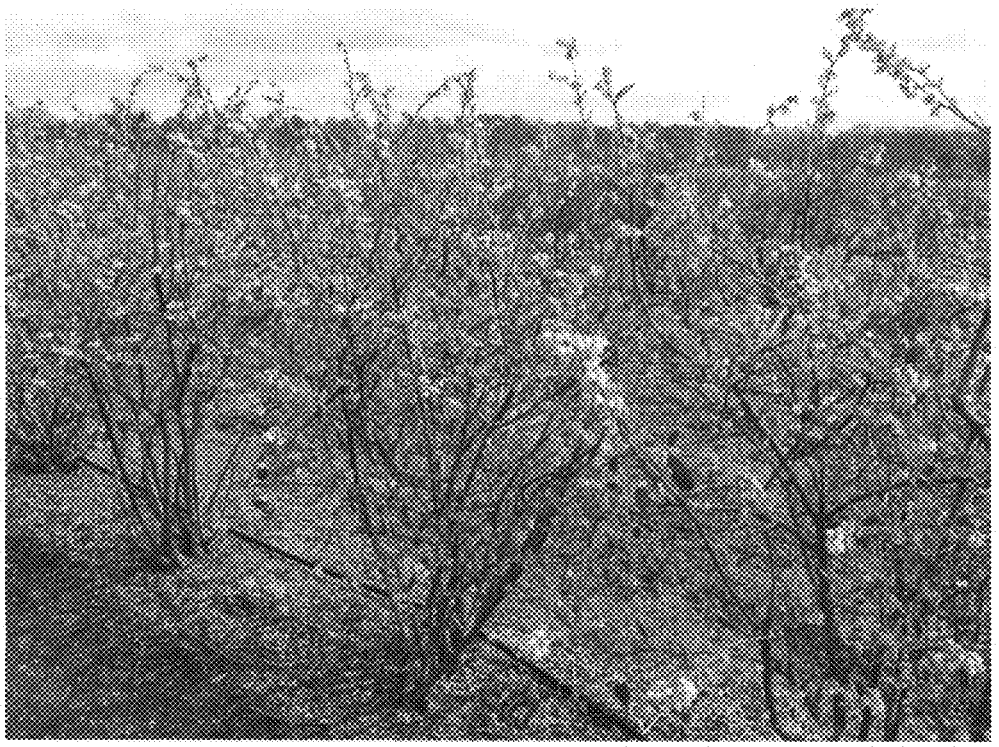
FIG. 1 is a photograph the new variety 'TH-906' during flowering in Griffin, Ga.
Figure 2:
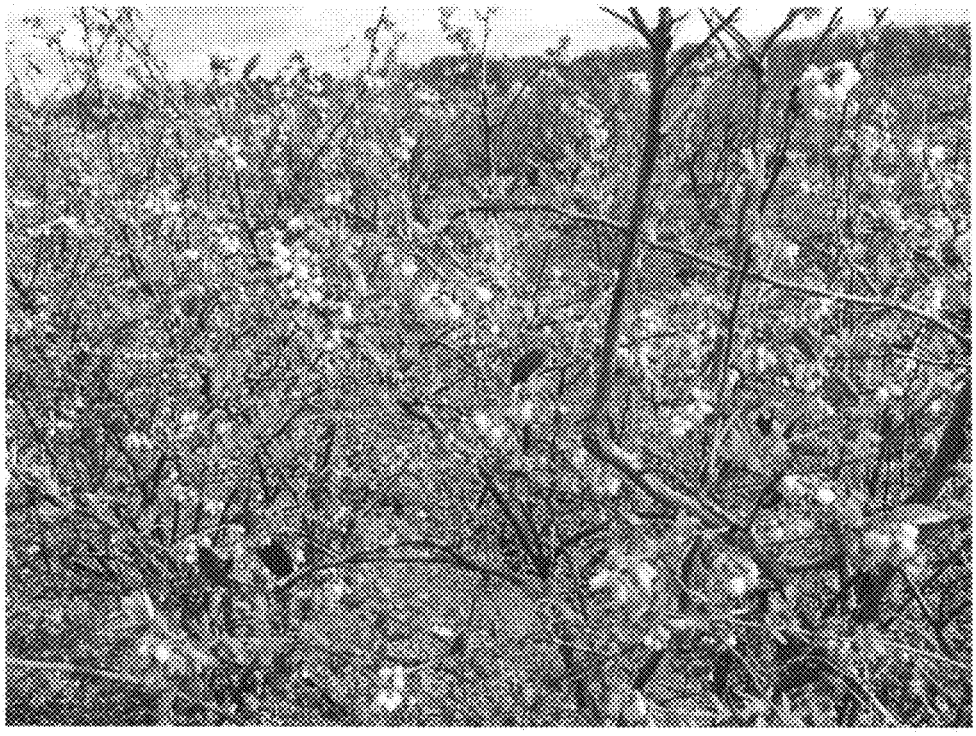
FIG. 2 is a close up photograph the new variety 'TH-906' during flowering in Griffin, Ga.
Figure 3:
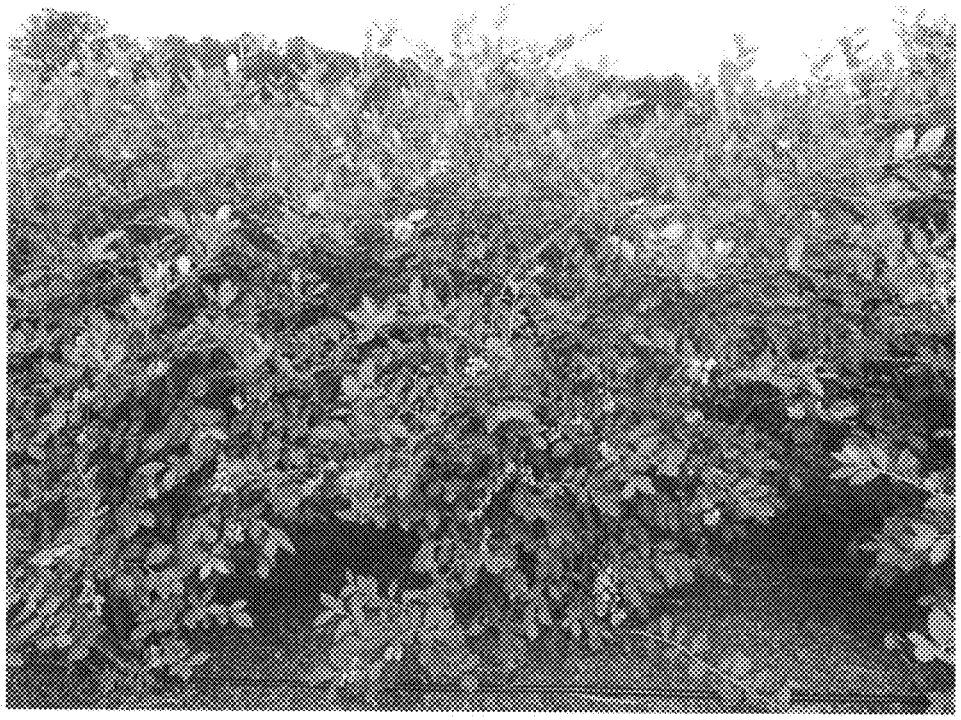
FIG. 3 is a photograph of new variety 'TH-906' during fruit ripening in Griffin, Ga.
Figure 4:
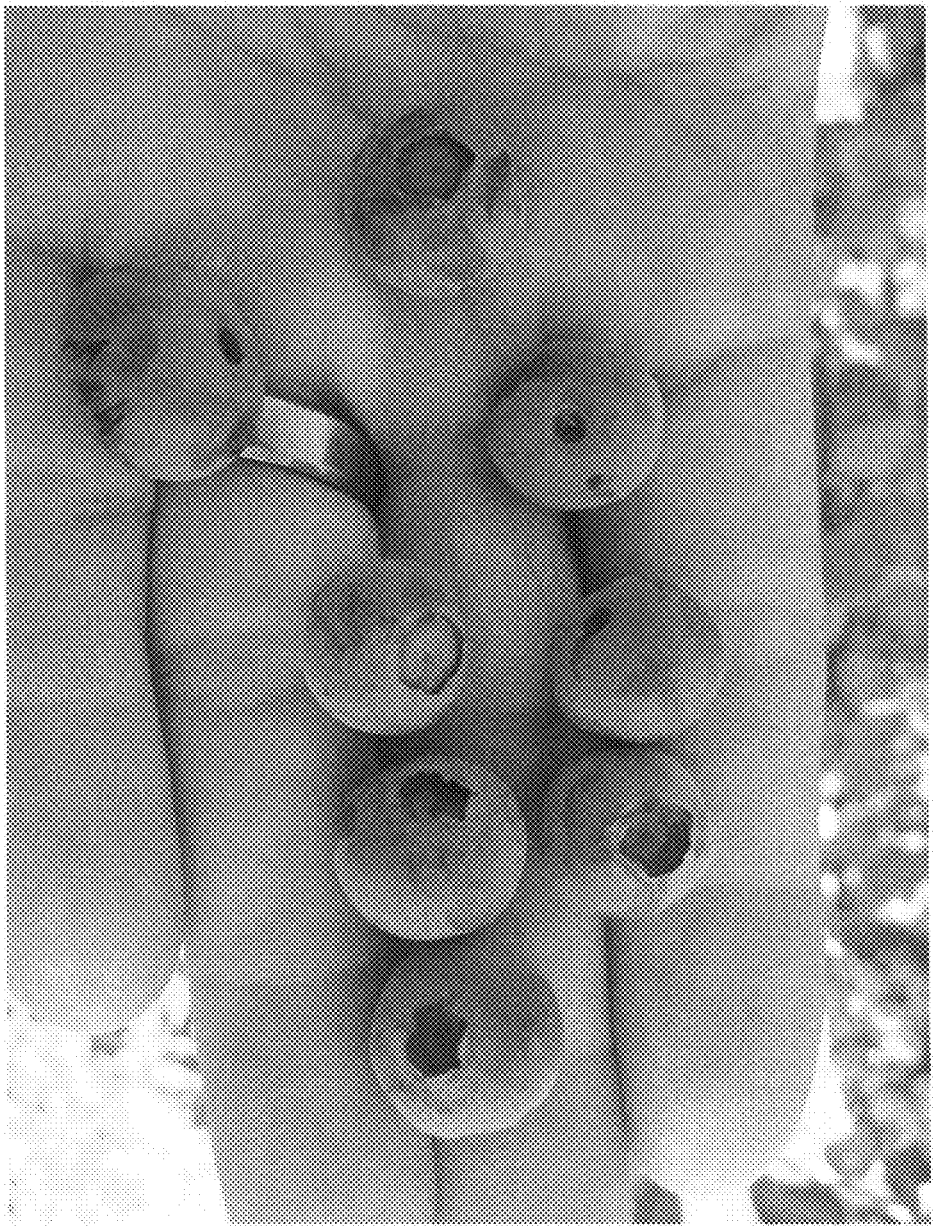
FIG. 4 is a photograph of typical fruit of the new variety 'TH-906'.

Throughout this specification, color names beginning with a small letter signify that the name of that color, as used in common speech, is aptly descriptive. Color names beginning with a capital letter designate values based upon the R.H.S. Colour Chart, 5$^{th}$ edition published by The Royal Horticultural Society, London, England.

The following is a detailed description of the botanical and pomological characteristics of the new variety 'TH-906'. Where dimensions, sizes, colors, and other characteristics are given, it is to be understood that such characteristics are approximations and averages set forth as accurately as practicable. The descriptions reported herein are largely from asexually propagated specimen plants grown in Alapaha and Griffin, Ga., with supplemental irrigation. The observed plants were about 5 to about 7 years old.

PLANT

Size: 2.2 to 2.5 m tall by about 5 years of age. The plant crown, or base, is narrow, typically 20 to 30 cm in diameter. Upper portion of plant canopy exceeds 1.8 to 2.2 m in diameter by 5 to 6 years.

Growth habit: Semi-upright, with 3 to 5 main canes arising from the crown and multiple branching of shoots from those canes beginning 15 to 25 cm above ground.

Growth: Highly vigorous.

Productivity: Medium to high yield, averaging 8 to 12 lbs of fruit per plant each year plants 5 years and older grown under well fertilized and irrigated field conditions.

Cold hardiness: Similar to other southern highbush cultivars such as 'Star' (U.S. Plant Pat. No. 10,675) and 'Camellia' (U.S. Plant Pat. No. 18,151).

Chilling requirement: Around 550 hours of temperatures at or below about 7° C. (about 45° F.) to induce normal leafing and flowering during the spring under conventional production systems. The chill requirement is similar to the female parent 'TH-653' (500 to 600 hours of chilling required), but more than the male parent 'Millennia' (350 or less hours of chilling is required.

Leafing: Plants tend to break sufficient leaf buds simultaneously with, or shortly after, anthesis.

Canes:

*Diameter.*—30 to 40 mm in plants that are about 5 years old and older. 20 to 25 mm in first major branch diameter. 10 to 15 mm in about 2 year old wood. 5 to 10 mm in current season wood.

*Color.*—Brown N200C in plants that are about 5 years old and older. Grey 201B in first major branch. Yellow Green 145B to Greyed Orange 177A in about 2 year old wood. Yellow Green 145B in current season wood.

Fruiting wood: Numerous twigs 20 to 25 cm in length, with internode lengths of 20 to 25 mm are common.

Disease resistance: No exceptional disease resistance or susceptibility observed; similar to southern highbush varieties 'Star' and 'Camellia'.

FOLIAGE

Leaf color: Healthy mature leaves.

*Top side.*—Green 137B, glaucous.

*Under side.*—Green 138D.

Leaf arrangement: Alternate, simple.

Leaf shape: Elliptic.

Leaf margins: Nearly entire, smooth.

Leaf venation: Pinnate, slightly reticulated.

Leaf apices: Broadly acute.

Leaf bases: Acute.

Leaf dimensions:

*Length.*—50 to 60 mm.

*Width.*—25 to 30 mm.

Petioles: Small.

*Length.*—4.0 to 6.5 mm.

*Width.*—1.5 to 2.0 mm.

*Color.*—Yellow Green 145C.

FLOWERS

Date of 50% anthesis: 5 year average March 8 in southeast Georgia; March 20 in middle Georgia.

Flower shape: Urceolate.

Flower bud number: High, averaging about 5 to 7 buds per cluster per fruiting season.

Flowers per cluster: 5 to 7 common.

Flower fragrance: Light rose fragrance noticed at times.

Corolla:

*Color.*—White N155B to White 155C (open flower).

*Length.*—8.0 to 9.0 mm.

*Width.*—7.0 to 8.5 mm.

*Aperture width.*—3.5 to 4.0 mm.

Flower peduncle:

*Length.*—9 to 12 mm.

*Color.*—Green 139D.

Flower pedicle:

*Length.*—4.5 to 5.0 mm.

*Color.*—Green 139D.

Calyx (with sepals):

*Diameter.*—6.0 to 7.0 mm.

*Color* (*sepals*).—Green RHS 138C.

Stamen:

*Length.*—6.0 to 7.0 mm.

*Number per flower.*—10.

*Filament color.*—Yellow-green 145D.

Style:

*Length.*—8.5 to 9.5 mm.

*Color.*—Yellow-green 145C.

Pistil:

*Length.*—10.0 to 12.0 mm.

*Ovary color* (*exterior*).—Green 138C.

Anther:

*Length.*—4.0 to 4.5 mm.

*Number.*—10.

*Color.*—Greyed-Orange 165A to Greyed-Orange 165B.

Pollen:

*Abundance.*—Medium.

*Color.*—Yellow White 158A.

Self-compatibility: The cultivar has demonstrated a moderate degree of self-compatibility.

FRUIT

Date of 50% maturity: May 12 (5 year average) in southeast Georgia, May 29 (5 year average) in middle Georgia.

Fruit development period: 65 to 70 days.

Berry color:

*With wax.*—Violet Blue 97B to Violet Blue 98D.

*With wax removed.*—Black 202A.

Berry surface wax abundance: High.

Berry flesh color: Green White 157B.

Berry weight:

*First harvest.*—1.6 g to 2.0 g.

*Second harvest.*—1.4 g to 1.7 g.

Berry size:

*Height from calyx to scar.*—10.0 to 14.0 mm.

*Diameter.*—16.0 to 18.0 mm.

Berry shape: Semi-spherical.

Fruit stem scar: Medium-size, medium-dry, little to no tearing at harvest.

Calyx: Depth 2.0 to 3.0 mm; width 5.0 to 8.0 mm; sepals not highly visible, inward and flat when present.

Berry firmness: Moderate to very firm.

Berry flavor and texture: Very sweet, mildly acidic flavor; smooth texture.

Storage quality: Good.

Suitability for mechanical harvesting: Not suited.

Uses: Most suitable for home gardens.

SEED

Seed abundance in fruit: Medium, with 10 to 20 fully developed seeds per berry.

Seed color: Greyed Orange 165B.

Seed dry weight: 41.0 mg per 100 seeds.

Seed size: 0.7 to 1.2 mm long; 0.5 to 0.8 mm wide for fully developed seeds.

What is claimed is:

1. A new and distinct variety of southern highbush blueberry plant named 'TH-906', substantially as illustrated and described herein.

* * * * *